United States Patent [19]

Drent

[11] 4,429,150
[45] Jan. 31, 1984

[54] MANUFACTURE OF ETHYLIDENE DIACETATE

[75] Inventor: Eit Drent, Amsterdam, Netherlands

[73] Assignee: Shell Oil Company, Houston, Tex.

[21] Appl. No.: 280,422

[22] Filed: Jul. 6, 1981

[30] Foreign Application Priority Data

Sep. 15, 1980 [GB] United Kingdom ................. 8029687

[51] Int. Cl.$^3$ ...................... C07C 67/36; C07C 67/37; C07C 69/16
[52] U.S. Cl. ................................. 560/232; 560/263; 562/517; 562/519; 568/484
[58] Field of Search ............... 560/232, 263, 114, 204; 562/517, 519

[56] References Cited

U.S. PATENT DOCUMENTS 3,213,155 10/1965 Shriesheim et al. ................ 562/496
4,252,741 2/1981 Porcelli et al. ...................... 560/232

FOREIGN PATENT DOCUMENTS 25702 3/1981 European Pat. Off. ............ 560/232
2016061 11/1970 Fed. Rep. of Germany ...... 560/263
1538782 1/1979 United Kingdom ................ 560/232

Primary Examiner—Vivian Garner
Attorney, Agent, or Firm—Ronald L. Clendenen; Ronald R. Reper

[57] ABSTRACT

Method for the manufacture of ethylidene diacetate by reacting methyl acetate and/or dimethyl ether with carbon monoxide and hydrogen in the presence of a catalyst comprising a Group VIII metal compound and a halogen-containing compound wherein the reaction is carried out in the presence of a sulphur-containing polar solvent.

1 Claim, No Drawings

MANUFACTURE OF ETHYLIDENE DIACETATE

BACKGROUND OF THE INVENTION

1. Field of the Invention

The present invention relates to a method for the manufacture of 1,1-diacetoxyethane (ethylidene diacetate) from methylacetate and/or dimethyl ether. 2. Background Abbreviations: The following abbreviations are utilized herein: EDA for ethylidene diacetate; MA for methyl acetate; and DME for dimethyl ether.

Ethylidene diacetate (EDA) is a valuable chemical which can be used as such (e.g. as solvent for chemical processes or compounds) as well as starting material for chemicals such as vinyl acetate or acetic acid anhydride.

It has been suggested in British specification No. 1,538,782, published Jan. 28, 1979, that EDA can be produced by carbonylation of methyl acetate (MA) and/or dimethyl ether (DME) in the presence of a Group VIII noble metal catalyst, a bromide or chloride and a promoter in the substantial absence of water. The reaction conditions as described in the above-mentioned specification lead, however, to the production of EDA with low selectivity. Moreover, a variety of by-products such as acetic acid anhydride and acetaldehyde are formed together with considerably more than the stoichiometrically expected amount of the less valuable acetic acid.

The presence of a promoter is considered essential for the process described in the aforementioned British patent specification. This is illustrated by the experiments described in Examples 5 and 8, respectively, wherein in the absence of a promoter no reaction products appear to have been formed at all under otherwise similar conditions.

Surprisingly, it has now been found that EDA can be produced with a good selectivity under mild process conditions when a sulphur-containing polar solvent is used. It should be noted that the sulphur-containing compounds used as solvent in the process according to the present invention cannot be considered as promoters, since their presence in promoter quantities in MA (the preferred solvent/reactant according to British patent specification No. 1,538,782) leads to an even lower selectivity than the promoters mentioned in the British patent specification. The use of other polar, non-sulphur-containing solvents such as acetonitrile and dimethyl formamide only leads to the production of acetic acid and various by-products.

SUMMARY OF THE INVENTION

The present invention relates to a method for the manufacture of ethylidene diacetate by reacting methyl acetate and/or dimethyl ether with carbon monoxide and hydrogen in the presence of a catalyst comprising a Group VIII metal compound and a halogen-containing compound wherein the reaction is carried out in the presence of a sulphur-containing polar solvent. Preferably the sulphur-containing polar solvent is a sulphone or sulphoxide of the following general formulas:

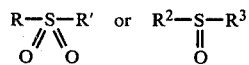

The reaction also may be advantageously carried in the presence of organo-phosphorus compound.

DESCRIPTION OF THE PREFERRED EMBODIMENTS

Normally the method according to the present invention will be carried out using methyl acetate as the starting material. It is also possible to use DME or mixtures of MA and DME as starting material. It would appear that DME will be converted primarily under the reaction conditions into MA by the introduction of a carbon monoxide moiety into the DME. If desired, the reaction according to the present invention can be carried out in two stages when DME is used as the starting material. Firstly, DME will be (partially) converted into MA, which in its turn, in the same or in a different vessel, will be converted into the final products EDA and acetic acid. It is further possible to use methanol as feedstock for the method according to the present invention, since this compound can be converted into DME or MA by methods known in the art. Mixtures of methanol, MA and/or DME can also by suitably applied.

The method according to the present invention can be carried out using a Group VIII metal compound as catalyst. Among Group VIII metal compounds rhodium and palladium compounds are preferred, but other Group VIII metal compounds such as iridium can also be used as well as combinations of various Group VIII metal compounds.

Examples of rhodium compounds comprise rhodium oxide, rhodium(III) hydroxide, rhodium(III) chloride, rhodium(III) chloride trihydrate, rhodium(III) bromide, rhodium(III) iodide as well as the corresponding pyridine and phosphine complexes such as tris(pyridine) rhodium(III) chloride or dichlorobis-(triphenylphosphine) rhodium, rhodium(III) formate, rhodium(III) acetate, rhodium(III) butyrate, rhodium(III) naphthenate, dirhodium octacarbonyl, tetrarhodium dodecacarbonyl, hexarhodium hexadecacarbonyl, rhodium dicarbonylacetyl acetonate and other organo-rhodium complexes. Preference is given to the use of rhodium(III) chloride trihydrate.

Examples of palladium compounds comprise palladium chloride, palladium chloride dihydrate, palladium bromide, palladium iodide, palladium oxide, or an organic palladium salt or complex such as palladium formate, palladium acetate, palladium butyrate and palladium acetyl acetonate. Preferred palladium compounds to be used in the process according to the present invention are palladium chloride, palladium chloride dihydrate and palladium acetate.

The amount of Group VIII metal compound to be used is not critical and any amount which exerts catalytic activity can be used. Amounts as low as about 0.001%w, calculated on MA (or precursor(s) thereof) can be used, preference being given to amounts in the range of from about 0.01–10%w, most preferably between about 0.05–5%w.

Suitable halogen-containing compounds comprise bromides and iodides such as alkyl bromides and alkyl iodides, especially methyl iodide; alkanoyl bromides and alkanoyl iodides such as acetyl bromide and acetyl iodide; hydrogen bromide and hydrogen iodide as well as compounds from which the above-mentioned compounds can be formed in situ. Examples of compounds which may generate suitable bromides and iodides comprise bromine and iodine as well as inorganic bromides and iodides such as alkali and alkaline earth metal and transition metal bromides and iodides such as sodium bromide, lithium iodide and chromium(III) iodide. Since the method according to the present invention is preferably carried out in the liquid phase, preference is given to those halogen-containing compounds which are compatible with the reactive environment, i.e. to alkyl bromides and alkyl iodides. Most preference is given to the use of methyl iodide.

The amount of halogen-containing compound to be used can vary between wide limits. In general, the use of an excess of halogen-containing compound over the Group VIII metal compound employed is preferred. Suitable molar ratios of halogen-containing compound to Group VIII metal compound are in the range of from about 200 to about 0.1, ratios in the range of from about 50 to about 5 being preferred. Also mixtures of compounds which can generate bromides or iodides and alkyl bromides or alkyl iodides can be suitably used in about the same molar ratios as defined hereinabove.

Sulphur-containing polar solvents which can be suitably used in the method according to the present invention comprise (a)cyclic sulphone and sulphoxides. Suitable sulphones may be represented by the general formula:

wherein R and $R^1$ represent the same or different aliphatic groups which may be joined together to form a cyclic sulphone.

Preferred acyclic sulphones are those according to the above formula wherein R and $R^1$ represent the same or different alkyl groups such as $C_1$ to $C_{12}$ alkyl groups. Specific examples include dimethyl, diethyl, dipropyl, dibutyl, methyl ethyl and methyl butyl sulphones.

Preferred cyclic sulphones and sulpholane and alkyl sulpholanes, such as those sulpholanes substituted by one or more $C_1$ to $C_8$ alkyl groups. Specific examples include 2-methyl sulpholane, 3-methyl sulpholane, 3-butyl sulpholane, 3-isopropyl sulpholane and 2-methyl-4-butyl sulpholane.

Suitable sulphoxides may be represented by the general formula:

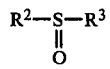

wherein $R^2$ and $R^3$, which may be the same or different, represent alkyl groups of up to 12 carbon atoms. Specific examples include dimethyl sulphoxide and diethyl sulphoxide.

The amount of sulphur containing polar solvent to be applied in the method according to the present invention may vary between wide limits. Generally the amount of solvent to be used should be at least half the molar amount of MA (and/or precursor(s) thereof) used, preference being given to solvent/MA ratios in the range of from about 1:2 to about 20:1, ratios between about 2:1 and about 5:1 being particularly preferred. If desired mixtures of sulphur-containing polar solvents may also be employed.

It has been found that the method according to the present invention can be carried out in the additional presence of organo-phosphorus compounds which are capable of forming a co-ordination compound with the Group VIII metal moiety present in the catalytic system used in the present method. It should be noted, however, that the presence of an organo-phosphorus compound in the absence of a sulphur-containing polar solvent or in the presence of a polar solvent such as dimethyl formamide does lead to a very low selectivity to EDA or even to no EDA being formed at all. Surprisingly, the additional presence of an organo-phosphorus compound in a sulphur-containing polar solvent leads to improved selectivity with respect to the production of EDA.

Examples of organo-phosphorus compounds which can be used conveniently comprise tertiary phosphines according to the general formula $PR^4R^5R^6$, wherein $R^4, R^5$ and $R^6$, which may be the same or different, each represent an alkyl, cycloalkyl or aryl group having up to 10 carbon atoms.

Preferred organophosphorus compounds comprise trimethyl phosphine, triethyl phosphine, tri-n-butyl phosphine and triphenyl phosphine. Also polyphosphorus compounds containing two or more phosphorus atoms interspaced with alkylene groups can be used. Examples of such compounds comprise bis(dihydrocarbyl phosphino) alkanes such as bis(diphenyl phosphino) methane, 1,2-bis(diphenyl phosphino) ethane and bis(dibutyl phosphino) methane.

The amount of organo-phosphorus compound additionally to be used in the method according to the present invention is generally related to the amount of Group VIII metal compound(s) present in the reaction mixture. Amounts ranging from about 0.1–100 times the molar amount of Group VIII metal compound(s) present can be suitably applied. Preference is given to the use of amounts up to about 10 times the molar amount of Group VIII metal compound(s) present.

The method according to the present invention can be carried out using a wide range of temperatures. Temperatures of up to about 300° C. can be suitably applied. Preference is given to temperatures in the range of from about 50° C. to about 200° C., most preferred temperatures are in the range between about 10° C. and about 150° C.

The method according to the present invention can be carried out using low pressures, e.g. pressures as low as about 5 bar. Pressures in the range of from about 20 to about 100 bar are preferred. Higher pressures, e.g. pressures as high as about 1000 bar can be applied, but they do not contribute substantially whilst the investment and energy costs involved increase considerably without compensating substantially in terms of product yield and/or selectivity.

According to the reaction equation wherein two molecules of MA are converted into one molecule of EDA and one molecule of acetic acid, carbon monoxide and hydrogen are consumed in a molar ratio of 2:1. It has been found, however, that without any substantial disadvantage wider molar ratios, e.g. ratios of from about 1:10 to about 10:1 can be applied. When starting from DME and/or methanol as feedstock, it may be advantageous to use an even higher carbon monoxide:-hydrogen molar ratio. Normally preference is given to the use of carbon monoxide:hydrogen ratios in the range of from about 2:1 to about 1:2.

The reaction time is not critical and will depend largely on the temperature and the pressure applied. Reaction times of from about 1 to about 20 hours are sufficient, preference being given to reaction times in the range of from about 5 to about 15 hours. Shorter or longer reaction times are not excluded, however.

The method according to the present invention can be carried out in the liquid as well as in the gaseous phase. Preference is given to the use of a liquid phase which enables a convenient introduction of carbon monoxide and hydrogen into the reaction vessel. If desired, carbon monoxide and hydrogen can be introduced together into the reaction vessel. The method according to the present invention can be carried out batchwise, semi-continuously or continuously. The reaction may comprise one or more autoclaves or one or more reactor tubes the walls of which are made of or coated with inert materials.

The reaction products may be worked up by techniques known in the art. For instance, the reaction product mixture comprising mainly EDA, acetic acid and unconverted MA (and/or precursors thereof) may be subjected to one or more (fractional) distillations to separate the main products EDA and acetic acid. The use of sulpholane as the solvent is especially advantageous in that it not only provides a good separation of the products, since its boiling point is much higher than that of the products obtained, but also allows for a (partial) recycle of the solvent when the method according to the present invention is carried out (semi-)continuously. If desired further purification treatment can be given to one or both separated products.

The present invention will now be illustrated by means of the following non-limiting Examples.

EXAMPLE I

The experiment was carried out in a 300 ml magnet-driven autoclave of Hastelloy C which contained 15 ml (0.2 mol) MA, 35 ml sulpholane, 1 mmol rhodium(III) chloride trihydrate and 30 mmol methyl iodide. The vessel was flushed with carbon monoxide and further charged with carbon monoxide (20 bar partial pressure) and hydrogen (partial pressure 20 bar). The autoclave was then heated to 135° C. and kept at this temperature for 3 hours. Thereafter the contents of the autoclave were allowed to cool and analysed using gas-liquid chromatography together with proton NMR. The conversion of MA amounted to 66% with a selectivity to EDA of 53%. (The selectivity has been defined by the ratio of EDA and acetic acid produced compared with the ratio to be produced according to the overall reaction equation as described hereinbefore).

EXAMPLE II

The experiment described in the previous Example was repeated using a smaller amount of methyl iodide (7 mmol). From GLC/NMR-analysis it appeared that the conversion amounted to 60% and the selectivity towards EDA was 50%.

EXAMPLE III

The experiment described in Example I was repeated using half of the original amount of rhodium(III) chloride trihydrate (0.5 mmol) and half the amount of methyl iodide (15 mmol). The reaction time was 7.5 hours. From GLC/NMR-analysis it appeared that the conversion of MA amounted to 75% and the selectivity towards EDA was 62%.

COMPARATIVE EXAMPLE A

The experiment described in Example I was repeated, but using sulpholane in a "promoter" quantity: 1 g sulpholane and 49 g MA as the solvent/starting material. The reaction time was 7.5 hours. From GLC/NMR-analysis it appeared that the conversion of MA amounted to 30% whereas the selectivity towards EDA was 5%. Apart from acetic acid, various unidentified products together with some propionic acid had been formed. It will be clear from this Example that sulpholane cannot be considered as exerting a "promoting" activity on the production of EDA from MA.

COMPARATIVE EXAMPLE B

The experiment described in Example I was repeated but using acetonitrile as the solvent. The reaction time was 7.5 hours. Although the conversion of MA was rather high (90%), EDA could not be detected in the reaction mixture as such. An excess of acetic acid and various unidentified products had been formed.

EXAMPLE IV

The experiment described in Example I was repeated during 15 hours using palladium acetate (0.7 mmol) as the catalyst under otherwise similar reaction conditions. From GLC/NMR-analysis the conversion of MA amounted to 50% and the selectivity of EDA was 60%.

EXAMPLE V

The experiment described in Example IV was repeated using 5 mmol triphenyl phosphine in addition to the catalyst under otherwise similar conditions. From GLC/NMR-analysis it appeared that the conversion of MA amounted to 25% but the selectivity to EDA was 86%.

EXAMPLE VI

The experiment described in Example III was repeated using triphenyl phosphine (3 mmol) in addition to the catalyst under otherwise similar conditions. From GLC/NMR-analysis it appeared that the conversion of MA amounted to 70% and the selectivity towards EDA was 91%.

COMPARATIVE EXAMPLE C

The experiment described in Example VI was repeated but using only MA as the starting material/solvent, no sulpholane being present, under otherwise similar reaction conditions. From GLC/NMR-analysis it appeared that the conversion of MA amounted to 20% and the selectivity towards EDA was 24%. Apart from acetic acid, acetaldehyde had also been formed. This comparative Example clearly illustrates that even in the presence of triphenyl phosphine (but in the absence of sulpholane) the selectivity towards EDA is very low indeed.

COMPARATIVE EXAMPLE D

The experiment described in comparative Example C was repeated using dimethyl formamide as the solvent (35 ml) and also using twice the amount of methyl iodide (30 mmol) under otherwise similar conditions. From GLC/NMR-analysis it appeared that the conversion of MA was low (20%) and no EDA could be detected at all. Again, acetic acid and large amounts of unidentified products had been formed.

EXAMPLE VII

The experiment described in Example VI was repeated using twice the amount of methyl iodide (30 mmol) and tri-n-butyl phosphine (3 mmol) in addition to the catalyst, under otherwise similar conditions. From GLC/NMR-analysis it appeared that the conversion of MA amounted to 90% and the selectivity to EDA was 80%.

EXAMPLE VIII

The experiment described in Example VI was repeated using methyl iodide in an amount of 30 mmol under otherwise similar conditions. From GLC/NMR it appeared that MA had been converted in an amount of 50%. The selectivity towards EDA was 97%. Acetic acid had been formed in almost the stoichiometrically expected amount.

EXAMPLE IX

The experiment described in the previous Example was repeated using 1,2-bis(diphenyl phosphino) ethane (1.5 mmol) in addition to the catalyst under otherwise similar conditions. From GLC/NMR-analysis it appeared that the conversion of MA amounted to 40% and the selectivity to EDA was 90%.

I claim:

1. A method for the manufacture of ethylidene diacetate by reacting methyl acetate and/or dimethyl ether with carbon monoxide and hydrogen in the presence of a catalyst comprising a Group VIII metal compound and a halogen-containing compound wherein the reaction is carried out at an elevated pressure of at least 5 bars and a temperature ranging from about 50° C. to about 200° C. in the presence of a sulphur-containing polar solvent which solvent comprises sulpholane.

* * * * *